United States Patent [19]

Chibata et al.

[11] 4,434,107

[45] Feb. 28, 1984

[54] PROCESS FOR PREPARING AN OPTICALLY ACTIVE P-HYDROXYPHENYLGLYCINE OR A SALT THEREOF

[75] Inventors: Ichiro Chibata, Suita; Shigeki Yamada, Toyonaka; Chikara Hongo, Osaka; Ryuzo Yoshioka, Kaizuka, all of Japan

[73] Assignee: Tanabe Seiyaku Co., Ltd., Osaka, Japan

[21] Appl. No.: 392,535

[22] Filed: Jun. 28, 1982

[30] Foreign Application Priority Data

Jul. 9, 1981 [JP] Japan ................................ 56-108008

[51] Int. Cl.$^3$ .................. C07C 143/30; C07C 101/72
[52] U.S. Cl. ............................... 260/501.12; 562/401
[58] Field of Search .................... 260/501.12; 562/401

[56] References Cited

U.S. PATENT DOCUMENTS 3,994,962 11/1976 Shirai et al. .................... 260/501.12
4,309,362 1/1982 Chibata et al. ................ 260/501.12

FOREIGN PATENT DOCUMENTS 78-28140 3/1978 Japan ................................. 562/400
78-103453 3/1978 Japan ................................. 562/400

Primary Examiner—James H. Reamer
Attorney, Agent, or Firm—Jordan B. Bierman; Linda Bierman

[57] ABSTRACT

The present invention relates to the optical resolution of a p-hydroxyphenylglycine salt with simultaneous racemization of the undesired enantiomer thereof. The invention is carried out by preferential crystallizing out the desired enantiomer from a supersaturated solution of the racemic modification thereof in a lower aliphatic acid in the presence of an aliphatic or aromatic aldehyde.

13 Claims, No Drawings

PROCESS FOR PREPARING AN OPTICALLY ACTIVE P-HYDROXYPHENYLGLYCINE OR A SALT THEREOF

This application claims priority under 35 U.S.C. 119 of Japanese Patent Application No. 108,008, filed July 9, 1981.

This invention relates to a process for preparing an optically active p-hydroxyphenylglycine or a salt thereof. More particularly, it relates to a simultaneous one stage resolution/racemization procedure for a p-hydroxyphenylglycine salt.

Optically active p-hydroxyphenylglycine, especially its D-enantiomer, is used as a starting material in the synthesis of semi-synthetic penicillins or cephalosporins.

Various methods have been known for preferential crystallization of an enantiomer of a p-hydroxyphenylglycine salt from a supersaturated solution of the racemic modification thereof. For example, the racemic modifications of p-hydroxyphenylglycine salts such as DL-p-hydroxyphenylglycine p-toluenesulfonate, DL-p-hydroxyphenylglycine o-toluenesulfonate, DL-p-hydroxyphenylglycine sulfosalicylate, DL-p-hydroxyphenylglycine benzenesulfonate or p-ethylbenzenesulfonate, DL-p-hydroxyphenylglycine 2-naphthol-6-sulfonate and DL-p-hydroxyphenylglycine $\beta$-naphthlenesulfonate can be resolved into each of their enantiomers by said preferential crystallization (U.S. Pat. Nos. 3,994,962 and 4,309,362, Japanese Patent Publication (unexamined) Nos. 28140/1978 and 103453/1978). The optical resolution of said racemic modifications have been conducted by the steps of making a supersaturated solution of the racemic modification of the p-hydroxyphenylglycine salt, adding crystals of an enantiomer of said salt to the supersaturated solution thereof, and then recovering the grown crystals of said optically active p-hydroxyphenylglycine salt. However, these known methods are still unsatisfactory. For example, in these known methods, only a small fraction of the desired enantiomer present in the supersaturated solution can be recovered by a single operation of said preferential crystallization, because only the desired enantiomer existing in the stable supersaturation state is crystallized. These methods are also disadvantageous in that the desired enantiomer must be separated promptly from the supersaturated solution before crystallization of the other enantiomer takes place, because otherwise the separated crystals of the desired enantiomer would be contaminated with the undesired enantiomer. A further disadvantage of these known methods is that it is necessary to carry out the preferential crystallization with respect to both of the desired and undesired enantiomer in order to make it possible to racemize said undesired enantiomer and use it again for the preferential crystallization.

As a result of various investigations, we have found that solutions of an optically active p-hydroxyphenylglycine salt can be racemized rapidly in the presence of an aliphatic acid and an aldehyde, even when suspended in a liquid medium crystals of an optically active p-hydroxyphenylglycine salt are stable enough and do not racemize under such racemization conditions of the dissolved p-hydroxyphenylglycine salt. We have also found that the preferential crystallization of either one of the enantiomers of a p-hydroxyphenylglycine salt can be accomplished from a supersaturated solution of the racemic modification thereof even under conditions that effect racemization of an optically active p-hydroxyphenylglycine salt dissolved in a liquid medium, insofar as said preferential crystallization is conducted in the presence of the aliphatic acid and the aldehyde. Thus, the present invention is to provide a method for preparing optically active p-hydroxyphenylglycine salt by preferentially crystallizing out either one of enantiomers of the p-hydroxyphenylglycine salt with simultaneous racemization of the other enantiomer. Apparently, this method makes it possible to convert all the racemic modification supplies into a desired enantiomer of the p-hydroxyphenylglycine salt, because the optical resolution of a DL-p-hydroxyphenylglycine salt takes place simultaneously with the racemization of an undesired enantiomer dissolved in liquid media and at the same time the crystals of the desired enantiomer once preferentially crystallized do not racemize under these conditions.

According to the present invention, an optically active p-hydroxyphenylglycine salt can be prepared by the steps of:

(a) forming a supersaturated solution of a DL-p-hydroxyphenylglycine salt in a lower aliphatic acid, said supersaturated solution also containing an aliphatic or aromatic aldehyde, (b) contacting said supersaturated solution with seed crystals of a desired enantiomer of the p-hydroxyphenylglycine salt at a temperature of not lower than 50° C., thereby allowing preferential crystallization of said desired enantiomer to take place from the supersaturated solution with simultaneous racemization of the other enantiomer dissolved therein.

The thus-grown crystals of the desired enantiomer is readily recovered from the supersaturated solution, and if required, the crystals of the optically active enantiomer thus recovered may be converted to optically active p-hydroxyphenylglycine in a conventional manner.

Any kind of DL-p-hydroxyphenylglycine salt which can be resolved into each of the enantiomers thereof by the preferential crystallization method can be used in the method of the present invention. Examples of such DL-p-hydroxyphenylglycine salt include the salt of DL-p-hydroxyphenylglycine with a sulfonic acid such as benzenesulfonic acid, p-toluenesulfonic acid, o-toluenesulfonic acid, sulfosalicylic acid, p-ethylbenzenesulfonic acid, 2-naphthol-6-sulfonic acid, $\beta$-naphthalenesulfonic acid and the like. Among these salts, the salts of DL-p-hydroxyphenylglycine with o-toluenesulfonic acid, p-toluenesulfonic acid or benzenesulfonic acid are especially preferred in the present invention. The above-mentioned DL-p-hydroxyphenylglycine salt may be prepared separately prior to using it for the simultaneous one stage resolution/racemization process; but, if required, both of DL-p-hydroxyphenylglycine and said sulfonic acid may be added to the resolution/racemization system individually so as to form the corresponding salt therein.

The aliphatic acid which can be used in the present invention includes, for example, a compound of the formula:

$$R^1\text{—COOH} \tag{I}$$

wherein $R^1$ is hydrogen or alkyl of one to 4 carbon atoms. Representative examples of such aliphatic acid include formic acid, acetic acid, propionic acid, butyric acid, valeric acid and the like. Among them, a preferred subgenus is the compound of the formula (I) in which $R^1$ is hydrogen or alkyl of one to 3 carbon atoms. More preferred subgenus is acetic acid and propionic acid. It is preferred to use 2 to 50 g of the aliphatic acid per g of the DL-p-hydroxyphenylglycine salt. When the aliphatic acid is used in the form of an aqueous solution thereof, the preferred concentration of said aliphatic acid in the solution is 10 to 100 v/v %, especially 60 to 100 v/v %.

On the other hand, examples of the aldehyde to be used in the present invention is a compound of the formula:

$$R^2\text{—CHO} \qquad (II)$$

wherein $R^2$ is hydrogen; alkyl of one to 6 carbon atoms such as methyl, ethyl, propyl, isopropyl, butyl, isobutyl, pentyl or hexyl; alkenyl of 2 to 4 carbon atoms such as vinyl, propenyl or butenyl; phenyl; phenyl having at least one substituent selected from the class consisting of hydroxy, nitro, amino and alkoxy of one to 4 carbon atoms (e.g., methoxy, ethoxy, propoxy or butoxy); phenylvinyl; oxygen-containing heteromonocyclic group such as furyl or nitrofuryl; and hydroxynaphthyl. Preferred examples of such aldehyde include formaldehyde, acetoaldehyde, propionaldehyde, n-butyraldehyde, isobutyraldehyde, n-valeraldehyde, caproaldehyde, n-heptylaldehyde, acrylaldehyde (i.e., acrolein), methacrylaldehyde (i.e., methacrolein), salicylaldehyde, m-hydroxybenzaldehyde, p-hydroxybenzaldehyde, o-nitrobenzaldehyde, m-nitrobenzaldehyde, 5-nitrosalicylaldehyde, anisaldehyde, o-aminobenzaldehyde, vaniline, naphtholaldehyde, phenylacrolein, furfural and nitrofurfural. Among these, a more preferred subgenus is the compound of the formula (II) in which $R^2$ is hydrogen; alkyl of one to 6 carbon atoms; vinyl; phenyl; phenyl having one to 3 substituent(s) selected from the class consisting of hydroxy, nitro and methoxy; and furyl. Another preferred subgenus is formaldehyde, acetoaldehyde, propionaldehyde, n-butyraldehyde, n-heptylaldehyde, acrolein, benzaldehyde, salicylaldehyde, p-hydroxybenzaldehyde, p-anisaldehyde, o-nitrobenzaldehyde, 5-nitrobenzaldehyde or furfural. A still further preferred subgenus is propionaldehyde, n-butyraldehyde, benzaldehyde and salicylaldehyde. It is preferred to use 0.001 to 0.5 mole, more preferably 0.005 to 0.2 mole, most preferably 0.01 to 0.2 mole, of the aldehyde per mole of the DL-p-hydroxyphenylglycine salt.

The supersaturated solution of the racemic modification of the present invention can be prepared by applying conventional procedures such as refrigeration, concentration, addition of an appropriate solvent or a combination of these operations to a solution of the DL-p-hydroxyphenylglycine salt. However, it is most convenient to prepare said supersaturated solution by cooling or concentrating a hot solution saturated with DL-p-hydroxyphenylglycine salt. For example, the supersaturated solution of the present invention can be obtained by dissolving the DL-p-hydroxyphenylglycine salt and the aldehyde in the lower aliphatic acid under refluxing, and cooling or concentrating the mixture. Additionally, the DL-p-hydroxyphenylglycine salt which is employed in preparing the supersaturated solution may not always be an equal mixture of the D- and L-enantiomers. Moreover, the lower aliphatic acid may be used alone in the simultaneous one stage resolution/racemization procedure of the present invention, but, if required, may be used as a mixture of said lower aliphatic acid and an inert solvent. Any inert solvent which is inactive to the DL-p-hydroxyphenylglycine salt, the lower aliphatic acid and the aldehyde and which can afford prompt crystallization of the desired enantiomer can be used for the purpose of the present invention. Examples of such inert solvent suitable for this purpose include water, benzene, toluene and the like.

When the supersaturated solution of the racemic modification is prepared as above, a small amount of crystals of one of the enantiomers of the p-hydroxyphenylglycine salt is added to the supersaturated solution as a seed, and the mixture is stirred at a temperature of not lower than 50° C. Preferential crystallization of one of the enantiomers (i.e., preferential crystallization of the desired enantiomer), corresponding to the enantiomer seeded, takes place during said operation. Moreover, during said operation, the undesired enantiomer of the p-hydroxyphenylglycine salt (i.e., the antipode of the enantiomer seeded) which remains dissolved in the supersaturated solution of the DL-p-hydroxyphenylglycine salt can be readily racemized under the abovementioned conditions insofar as the preferential crystallization is carried out in the presence of the lower aliphatic acid and the aldehyde. The crystals of the desired enantiomer once crystallized by said preferential crystallization are stable even when suspended in the liquid medium and do not racemize under such racemization conditions of the dissolved p-hydroxyphenylglycine salt. Thus, the method of the present invention makes it possible not only to carry out the preferential crystallization of the desired enantiomer from the supersaturated solution with simultaneous racemization of the undesired enantiomer dissolved therein, but also to convert all of the undesired enantiomer into the desired enantiomer because such undesired enantiomer is racemized simultaneously with the preferential crystallization and again utilized as the starting material of said preferential crystallization of the desired enantiomer. Further, since the undesired enantiomer is continuously converted to the desired enantiomer by means of racemization and preferential crystallization, it becomes possible to effect high recovery of the desired enantiomer by quite simple operations without spontaneous crystallization of said undesired enantiomer. It is preferred to carry out such simultaneous one stage resolution/racemization procedure of the present invention at a temperature of not lower than 50° C., more preferably 50° to 120° C., most preferably 80° to 110° C. The seed crystals to be used in the present invention should have a high optical purity. The greater the amount of the seed, the better the resultant resolution. The practical proportion of the seed crystals to be added is generally within the range of about 0.5 to 5 w/w % based on the weight of the DL-p-hydroxyphenylglycine salt used as the starting material. In this respect, however, it should be noted that, once the desired enantiomer starts crystallizing out preferentially from the supersaturated solution, it is not essential to add the seed crystals of the desired enantiomer thereto. This is because the crystals of the desired enantiomer which is crystallized by said preferential crystallization also serves as the seed crystals. If required, the simultaneous one stage resolution/racemization procedure of the present invention may be carried out in the presence of a free α-amino acid to promote racemization of the enantiomer of p-hydroxyphenylglycine salt (i.e., the undesired enantiomer) which remains dissolved in the liquid medium. Any kinds of free α-amino acids may be used for this purpose, and said free α-amino acid may be either an optically active enantiomer or racemic modification thereof. Examples of the free α-amino acids to be used in the present invention include a neutral free α-amino acid such as glycine, alanine, valine, isoleucine, serine, threonine, cystine, cysteine, methionine, tryptophan, phenylalanine, tyrosine, dopa (i.e., 3-(3,4-dihydroxyphenyl)alanine), phenylglycine or p-hydroxyphenylglycine; a basic free α-amino acid such as arginine, lysine, ornithine or histidine; an acidic free α-amino acid such as aspartic acid or glutamic acid; and an free α-imino acid such as proline or hydroxyproline. Generally, however, it is especially preferred to use p-hydroxyphenylglycine as said free α-amino acid because in this case the preferential crystallization of the desired enantiomer of the p-hydroxyphenylglycine salt can be carried out without contamination with unlike amino acids. It is preferred to use the free α-amino acid in an amount of about 0.1 to 3 w/w % based on the weight of the DL-p-hydroxyphenylglycine salt to be used as the starting material.

The above-mentioned simultaneous resolution/racemization process of the present invention can be carried out batchwise. However, said method of the invention is especially suitable to carry out in a continuous manner, because the supersaturated solution of the racemic modification can be readily made continuously by feeding the DL-p-hydroxyphenylglycine salt to the reaction system in a conventional manner. For example, even when the supersaturation of the solution of the racemic modification is depleted by preferential crystallization of the desired enantiomer and simultaneous racemization of the undesired enantiomer, the same conditions as the previous operation is obtained without the separation of the desired enantiomer crystallized by dissolving in said solution a certain amount of the racemic modification which is substantially equal to the amount of the desired enantiomer previously crystallized. Said dissolution of the racemic modification in the solution can of course be effected in a conventional manner such as heating. The supersaturated solution of the racemic modification may also be made afresh by suspending free DL-p-hydroxyphenylglycine to the solution of the racemic modification of the p-hydroxyphenylglycine salt and then adding an acid thereto to form the corresponding p-hydroxyphenylglycine salt therein. Alternatively, such operations as cooling, concentration, addition of a solvent or a combination thereof may be used for making the supersaturated solution of the racemic modification. Thus, the preferential crystallization and simultaneous racemization is repeated indefinitely, and the racemic modification which is supplied can be successfully and entirely converted to the desired enantiomer of the p-hydroxyphenylglycine salt, i.e., the enantiomer corresponding to the one seeded.

After the above-mentioned operations, the desired enantiomer of the p-hydroxyphenylglycine salt thus obtained can be recovered by a conventional manner, for example, by filtration, centrifugation and the like. Moreover, if required, the desired enantiomer of the p-hydroxyphenylglycine salt can be converted into its free form by treating it with an alkali agent or an ion-exchange resin.

According to the method of the present invention, racemization of the undesired enantiomer of the p-hydroxyphenylglycine salt takes place simultaneously with the preferential crystallization of the desired enantiomer, and all of the racemic modification of the p-hydroxyphenylglycine salt existing in the supersaturation state can be converted to the desired enantiomer thereof. Thus, as compared with the known methods for optical resolution of the p-hydroxyphenylglycine salts, the method of the present invention is quite advantageous in that it makes it unnecessary to conduct the preferential crystallization of the undesired enantiomer of the p-hydroxyphenylglycine salt, whereas in the known methods the preferential crystallization of the desired and undesired enantiomers must always be conducted alternately (In the known methods, once the preferential crystallization of the desired enantiomer is carried out, it is a must to remove the undesired enantiomer from the supersaturated solution prior to repeating the preferential crystallization of the desired enantiomer.) In addition, the preferential crystallization of an enantiomer of the p-hydroxyphenylglycine salt in the known methods is sometimes accompanied with spontaneous crystallization of its antipode. The method of the present invention is free from this disadvantage because the undesired enantiomer which remains dissolved in the solution is continuously converted to the desired enantiomer by means of preferential crystallization and racemization during the operations. Therefore, as is apparent from these facts, the method of the present invention is quite useful and advantageous for preparation of optically active p-hydroxyphenylglycine or its salt in an industrial scale.

EXAMPLE 1

27.2 g of DL-p-hydroxyphenylglycine benzenesulfonate and 1.1 ml of n-butyraldehyde are dissolved in 100 ml of aqueous 95 V/V % acetic acid under reflux. 0.6 g of glycine is added thereto, and the mixture is kept at 100° C. Then, 0.4 g of D-p-hydroxyphenylglycine benzenesulfonate is added as seed crystals to said mixture, and the mixture is stirred at the same temperature for 90 minutes. Crystalline precipitates are collected by filtration, washed with acetic acid and then dried. 2.6 g of D-p-hydroxyphenylglycine benzenesulfonate are obtained.

$[\alpha]_D^{25} - 67.5°$ (C=1, H$_2$O)

Optical purity: 98.0%

The mother liquor obtained in the above-mentioned operation shows no substantial optical activity, and 20.2 g of DL-p-hydroxyphenylglycine benzenesulfonate ($[\alpha]_D^{25} \pm 0.0°$ (C=1, H$_2$O)) are recovered therefrom by cooling, followed by filtration of crystalline precipitates.

It is clear from this fact that L-p-hydroxyphenylglycine benzenesulfonate, i.e., an antipode of the enantiomer seeded to the mixture, is completely racemized in the liquid phase during the operation.

EXAMPLE 2

38.0 g of DL-p-hydroxyphenylglycine p-toluenesulfonate and 1.3 ml of salicylaldehyde are dissolved in 100 ml of aqueous 95 V/V % acetic acid under reflux. 0.8 g of glycine is added thereto, and the mixture is kept at 100° C. 0.4 g of D-p-hydroxyphenylglycine p-toluenesulfonate is added as seed crystals to said mixture, and the mixture is stirred at the same temperature for 90 minutes. Crystalline precipitates are collected by filtration, washed with acetic acid and then dried. 3.1 g of D-p-hydroxyphenylglycine p-toluenesulfonate are obtained.

$[\alpha]_D^{25} -64.6°$ (C=1, H$_2$O)

Optical purity: 97.1%

The mother liquor obtained in the above-mentioned operation shows no substantial optical activity, and 17.7 g of DL-p-hydroxyphenylglycine p-toluenesulfonate ($[\alpha]_D^{25} \pm 0.0°$ (C=1, H$_2$O)) are recovered therefrom by cooling, followed by filtration of crystalline precipitates.

It is clear from this fact that L-p-hydroxyphenylglycine p-toluenesulfonate, i.e., an antipode of the enantiomer seeded to the mixture, is completely racemized in the liquid phase during the operation.

EXAMPLE 3

19.0 g of DL-p-hydroxyphenylglycine o-toluenesulfonate and 1.0 ml of benzaldehyde are dissolved in aqueous 95 V/V % acetic acid under reflux, and the mixture is kept at 100° C. 5.0 g of DL-p-hydroxyphenylglycine are suspended to said mixture and then 1.0 g of D-p-hydroxyphenylglycine o-toluenesulfonate is added as seed crystals to the mixture. A solution of 5.0 g of o-toluenesulfonic acid dihydrate in 5 ml of acetic anhydride is added to the mixture over a period of 1.5 hours under stirring. During the addition, the crystals of DL-hydroxy-phenylglycine added above dissolves therein. The mixture is further stirred at the same temperature for one hour. Crystalline precipitates are collected by filtration, whereby 9.7 g of D-p-hydroxyphenylglycine o-toluenesulfonate are obtained.

$[\alpha]_D^{25} -64.1°$ (C=1, H$_2$O)

Optical purity: 96.2%

The mother liquor obtained in the above-mentioned operation shows no substantial optical activity, and 13.7 g of DL-p-hydroxyphenylglycine o-toluenesulfonate ($[\alpha]_D^{25} \pm 0.0°$ (C=1, H$_2$O)) are recovered therefrom by cooling, followed by filtration of crystalline precipitates.

It is clear from this fact that the preferential crystallization of D-p-hydroxyphenylglycine o-toluenesulfonate, i.e., a seeded isomer, and the racemization of L-p-hydroxyphenylglycine o-toluenesulfonate, i.e., an antipode of the enantiomer seeded to the mixture, took place simultaneously.

EXAMPLE 4

27.2 g of DL-p-hydroxyphenylglycine benzenesulfonate and 1.3 ml of salicylaldehyde are dissolved in 100 ml of aqueous 95 V/V % acetic acid under reflux. 0.6 g of glycine is added to the mixture, and the mixture is kept at 100° C. 2.0 g of D-p-hydroxyphenylglycine benzenesulfonate are added as seed crystals to said mixture, and the mixture is stirred at the same temperature for one hour. 2.0 g of powdered DL-p-hydroxyphenylglycine benzenesulfonate are added to the mixture, and the mixture is stirred at 113° C. (outer bath) for 10 minutes to dissolve only the racemic modification therein. 0.6 ml of salicylaldehyde is added to the mixture, and the mixture is stirred at 100° C. for one hour. Then, after 2.0 g of the crystals of DL-p-hydroxyphenylglycine benzenesulfonate are further dissolved in the mixture, 0.6 ml of salicylaldehyde is added thereto. The mixture is stirred at 100° C. for one hour. Crystalline precipitates are collected by filtration, whereby 8.3 g of DL-p-hydroxyphenylglycine benzenesulfonate are obtained.

$[\alpha]_D^{25} -67.4°$ (C=1, H$_2$O)

Optical purity: 97.8%

19.3 g of DL-p-hydroxyphenylglycine benzenesulfonate are recovered from the mother liquor obtained above.

$[\alpha]_D^{25} \pm 0.0°$ (C=1, H$_2$O)

EXAMPLE 5

(1) 19.0 g of DL-p-hydroxyphenylglycine o-toluenesulfonate are dissolved in 100 ml of aqueous 95 V/V % acetic acid under reflux, and the solution is kept at 100° C. 1.3 ml of salicylaldehyde are added to the solution, and 51.0 g of the crystals of DL-p-hydroxyphenylglycine are suspended therein. After 10 minutes, 2.0 g of D-p-hydroxyphenylglycine o-toluenesulfonate are added as seed crystals to the mixture under stirring. A solution of 62.5 g of o-toluenesulfonic acid dihydride in 62.5 ml of acetic anhydride is poured into the mixture at the rate of 5.0 ml/hr. Five and twenty hours after addition of the seed crystals, 1.3 ml and 0.7 ml of salicylaldehyde are added to the mixture, respectively. Then, the mixture is stirred at the same temperature for 2 hours. Crystalline precipitates are collected by filtration, whereby 82.8 g of D-p-hydroxyphenylglycine o-toluenesulfonate are obtained.

$[\alpha]_D^{25} -64.9°$ (C=1, H$_2$O)

Optical purity: 97.4%

After the mother liquor obtained above is cooled at room temperature, crystalline precipitates are collected by filtration. 18.2 g of DL-p-hydroxyphenylglycine o-toluenesulfonate are recovered.

$[\alpha]_D^{25} \pm 0.0°$ (C=1, H$_2$O)

(2) 82.8 g of D-hydroxyphenylglycine o-toluenesulfonate obtained in paragraph (1) are dissolved in 230 ml of water under heating. The solution is adjusted to pH 6 with an aqueous sodium hydroxide solution, and the solution is stirred under ice-cooling. Crystalline precipitates are collected by filtration, whereby 34.7 g of D-p-hydroxyphenylglycine are obtained.

$[\alpha]_D^{25} -158.2°$ (C=1, N-HCl)

What we claim is:

1. A process for preparing an optically active p-hydroxyphenylglycine salt which comprises the steps of:
  (a) forming a supersaturated solution of the racemic modification of a p-hydroxyphenylglycine salt selected from the class consisting of p-hydroxyphenylglycine benzenesulfonate, p-hydroxyphenylglycine p-toluenesulfonate, p-hydroxyphenylglycine o-toluenesulfonate, p-hydroxyphenylglycine sulfosalicylate, p-hydroxyphenylglycine p-ethylbenzenesulfonate, p-hydroxyphenylglycine 2-naphthol-6-sulfonate and p-hydroxyphenylglycine β-naphthalenesulfonate in a lower aliphatic acid of the formula:

$$R^1-COOH \qquad (I)$$

wherein $R^1$ is hydrogen or alkyl having one to 4 carbon atoms, said lower aliphatic acid being present in an amount of about 2 to about 50 g per g of said p-hydroxyphenylglycine salt, said supersaturated solution also containing an aliphatic or aromatic aldehyde of the formula:

$$R^2-CHO \qquad (II)$$

wherein $R^2$ is hydrogen; alkyl having one to 6 carbon atoms; alkenyl having 2 to 4 carbon atoms; phenyl; phenyl having at least one substituent selected from the class consisting of hydroxy, nitro, amino and alkoxy of one to 4 carbon atoms; phenylvinyl; oxygen-containing heteromonocyclic group; and hydroxynaphthyl, said aldehyde being present in an amount of 0.001 to 0.5 mole per mole of DL-p-hydroxyphenylglycine salt, and (b) contacting said supersaturated solution with seed crystals of a desired enantiomer of said p-hydroxyphenylglycine salt at a temperature not lower than 50° C., thereby allowing preferential crystallization of said desired enantiomer to take place from said supersaturated solution with simultaneous racemization of the other enantiomer dissolved therein.

2. The process of claim 1, further comprising the step of recovering the desired enantiomer from the supersaturated solution.

3. The process of claim 1, wherein said p-hydroxyphenylglycine salt is p-hydroxyphenylglycine benzenesulfonate, p-hydroxyphenylglycine p-toluenesulfonate or p-hydroxyphenylglycine o-toluenesulfonate.

4. The process according to claim 1, wherein said aliphatic acid is selected from the class consisting of formic acid, acetic acid, propionic acid, butyric acid and valeric acid, and said $R^2$ is hydrogen; alkyl having one to 6 carbon atoms; vinyl; phenyl; phenyl having at least one substituent selected from the class consisting of hydroxy, nitro and methoxy; or furyl.

5. The process according to claim 1, 2, 3 or 4, wherein the aliphatic acid is formic acid, acetic acid or propionic acid, and the aliphatic or aromatic aldehyde is formaldehyde, acetaldehyde, propionaldehyde, n-butyraldehyde, n-heptylaldehyde, acrolein, benzaldehyde, salicylaldehyde, p-hydroxybenzaldehyde, p-anisaldehyde, o-nitrobenzaldehyde, 5-nitrosalicylaldehyde of furfural.

6. The process according to claim 1, 2, 3 or 4, wherein the aliphatic acid is used in the form of a mixture thereof with water, benzene or toluene.

7. The process according to claim 1, 2, 3 or 4, wherein said supersaturated solution is contacted with said seed crystals of the desired enantiomer at 50° to 120° C.

8. The process according to claim 1, 2, 3 or 4, wherein the aliphatic or aromatic aldehyde is used in an amount of 0.01 to 0.2 moles per mole of the DL-p-hydroxyphenylglycine salt.

9. The process according to claim 1, 2, 3 or 4, wherein said contacting occurs in the presence of a free -amino acid.

10.

The process according to claim 9, wherein the free -amino acid is glycine or p-hydroxyphenylglycine.

11. The process according to claim 9, wherein the free α-amino acid is used in an amount of 0.001 to 0.8 moles per mole of the DL-p-hydroxyphenylglycine salt.

12. The process according to claim 1, 2, 3 or 4, wherein simultaneous one stage resolution/racemization is carried out continuously by feeding
(1) DL-p-hydroxyphenylglycine and an acid capable of forming, with DL-p-hydroxy phenylglycine, said DL-p-hydroxy phenylglycine salt, or
(2) additional DL-p-hydroxyphenylglycine salt to said supersaturated solution.

13. The process according to claim 2, further treating the recovered enantiomer with an alkali or an ion-exchange resin to give an optically active enantiomer of free p-hydroxyphenylglycine.

* * * * *